United States Patent [19]
Fleischmann

[11] Patent Number: 6,117,111
[45] Date of Patent: *Sep. 12, 2000

[54] DEVICE FOR SEALING AN INJURY AREA

[76] Inventor: Wim Fleischmann, Nelkenweg 15, D-89182 Bernstadt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/809,395

[22] PCT Filed: Sep. 18, 1995

[86] PCT No.: PCT/DE95/01292

§ 371 Date: Mar. 20, 1997

§ 102(e) Date: Mar. 20, 1997

[87] PCT Pub. No.: WO96/09022

PCT Pub. Date: Mar. 28, 1996

[30] Foreign Application Priority Data

Sep. 20, 1994 [DE] Germany .............................. 44 33 450

[51] Int. Cl.[7] .............................. A61M 5/32; A61F 13/00
[52] U.S. Cl. .............................................. 604/180; 602/52
[58] Field of Search ..................................... 604/180, 174, 604/305, 307, 336–338, 355; 602/42, 43, 58, 52, 54, 79; 128/112.1, 113.1; 600/581

[56] References Cited

U.S. PATENT DOCUMENTS

| | | | |
|---|---|---|---|
| 3,805,789 | 4/1974 | Marsan | 128/283 |
| 3,954,105 | 5/1976 | Nordby et al. | 128/275 |
| 4,166,051 | 8/1979 | Cilento et al. | 260/17.4 |
| 4,743,232 | 5/1988 | Kruger | 604/180 |
| 4,871,812 | 10/1989 | Lucast et al. | 525/186 |
| 4,909,244 | 3/1990 | Quarfoot et al. | 604/304 |
| 4,969,881 | 11/1990 | Viesturs | 604/305 |
| 5,120,813 | 6/1992 | Ward, Jr. | 528/28 |
| 5,236,421 | 8/1993 | Becher | 604/180 |
| 5,322,695 | 6/1994 | Shah et al. | 602/52 |
| 5,447,492 | 9/1995 | Cartmell et al. | 602/58 |
| 5,489,262 | 2/1996 | Cartmell et al. | 602/57 |
| 5,569,207 | 10/1996 | Gisselberg et al. | 604/175 |
| 5,571,079 | 11/1996 | Bello et al. | 602/46 |
| 5,636,643 | 6/1997 | Argenta et al. | |
| 5,645,081 | 7/1997 | Argenta et al. | |
| 5,674,523 | 10/1997 | Cartmell et al. | 424/445 |
| 5,685,859 | 11/1997 | Kornerup | 604/180 |
| 5,695,456 | 12/1997 | Cartmell et al. | 602/43 |
| 5,762,620 | 6/1998 | Cartmell et al. | 602/42 |

FOREIGN PATENT DOCUMENTS

| | | | |
|---|---|---|---|
| 0 117 714 | 9/1984 | European Pat. Off. | A61F 13/02 |
| 3443101 | 4/1974 | Germany . | |
| 40 12 232 A1 | 10/1991 | Germany | A61F 13/02 |
| 470 878 | 5/1969 | Switzerland | A61F 13/02 |
| WO 89/02259 | 3/1989 | WIPO . | |
| WO 90/11795 | 10/1990 | WIPO . | |
| WO 93/09727 | 5/1993 | WIPO . | |

*Primary Examiner*—Sharon Kennedy
*Attorney, Agent, or Firm*—Pendorf & Cutliff

[57] ABSTRACT

In order to seal it off, an injury area (12) is covered by a water-vapour-permeable, airtight foil (18). An easily deformable, non flowing sealing material (22), preferably a silicone or a hydrogel, is used to provide an airtight leak seal between the surface of the skin (10) and the foil (18). The sealing means (22) makes it possible in particular to seal the passage of a drain (16) between the surface of the skin (10) and the foil (18).

5 Claims, 3 Drawing Sheets

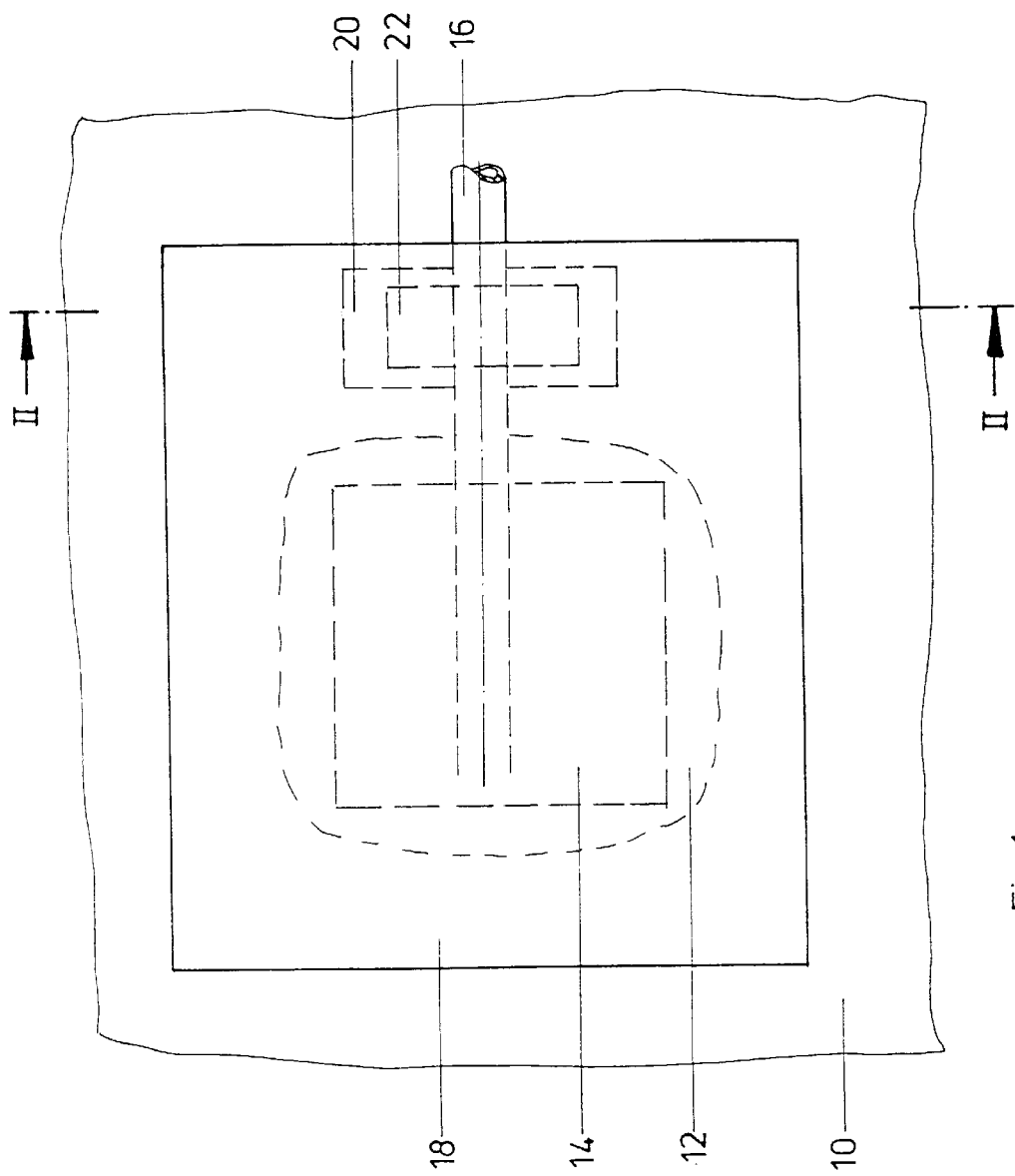

DEVICE FOR SEALING AN INJURY AREA

BACKGROUND OF THE INVENTION

1. Field of the Invention

The invention is concerned with a device for sealing off an injury area.

2. Description of the Related Art

From WO93/09 727 it is known to cover injury areas such as for example, fresh or chronic wounds, burns, caustic burns and the like with a water-vapor-permeable airtight foil. This foil is adhered completely around the wound area on the outer surface of the skin, in order to form an air-tight seal of the wound area. By means of a drain provided in the injury area under the foil, an under-pressurization is achieved in the wound area. In particular in large and deep wounds a porous foam insert can be provided in the wound, within which the drain is included, in order to evacuate a large surface area of the injury area and to siphon off the wound secretions.

If in accordance with this known device the drain is provided on the skin outer surface below the foil, so there results in the area of the drain a loss of seal between the skin outer surface and the foil which complicates or prevents the achievement or maintenance of the desired under-pressurization. It is thus the normal practice, that the drain is directed from the injury area through the body tissue and exits through the skin surface outside of the foil. This method is associated with a supplemental injury, which carries with it a risk of infection. Besides this the pulling of the drain tube through the tissue is not possible without anesthetics, so that the process is not very suitable for the ambulatory application and the emergency care.

SUMMARY OF THE INVENTION

The invention is concerned with the task, of providing a device for sealing off a wound area, with which a simple and reliable air-tight closing off of the wound area is made possible.

The invention is based upon the idea, of utilizing an easily deformable, non-flowing sealing material, in order to form leak-proof seals in the unsealed areas between the foil covering the wound area and the skin surface. This sealing material, which is preferably a silicone, a hydro-colloid or a lyogel, in particular a hydrogel, is easily deformable by hand and adapts to the unevenness in the skin or also the wrinkles or folds in the foil, such that the sealing material penetrates into any unsealed areas which may be present and closes these off. The deformability and the flowability characteristics of the sealing material are so selected, that an easy deformability and a good penetration in unsealed areas is obtained; however, a flowing out of the sealing material under the influence of the operational pressure gradients is ruled out.

In the case that a vacuum sealing of the wound is undertaken, then the drain used for siphoning off of the skin surface can be directed or channeled out under the foil, whereby the sealing material encloses the drain and the area around the drain between the foil and the skin outer surface and forms an air-tight seal by filling in these interstitial spaces.

In the sealing off of a large surface area of the body surface, such as for burns, for accidents and the like, which in particular is essential for primary emergency care, it is difficult to provide the covering foil upon the bodily outer surface without any folds or wrinkles and therewith flush upon the skin and to achieve adhesion. Here the sealing material offers the possibility, of providing a sealing between the foil and the skin outer surface, even over uneven features of the body outer surface, and in folds or wrinkles of the foil. For this a strip of the sealing material is deposited along the edge or rim of the foil to be used for covering, between the skin outer surface and the foil. In accordance herewith, the foil can in particular also be formed into a tube or a sack-like construction, in order for example to encase or surround an extremity of the patient. The rim of the sack shaped foil to be sealed or, as the case may be, the two rims of the tubular foil to be sealed, can be sealed using an extremity encompassing band shaped strip of the sealing material. In given cases even in such applications a drain can be introduced under the foil and sealed by means of the sealing material.

In order to maintain the appropriate adjustment of the deformability and the flowability characteristics suitable for the application of the sealing material, it is necessary to maintain the moisture content of the sealing material during storage. For this the sealing material can be kept in the ready condition in a tube or a pouch, so that the sealing material can be extruded on demand on the desired area from out of the tube or pouch. A design which is convenient for many applications is comprised therein, that the sealing material is provided in ready to use condition in the form a strips or sheets, which are tightly sealed by a foil wrapper or in a tightly sealed container. The foil wrapper can be designed to be peeled off, in order that the sealing material can be applied after peeling off of the sealing foil. It is also possible, that the sealing material is permanently enclosed in the sealing foil. In this case the sealing foil is preferably provided with an adhesive outer layer, such that the sealing material can be adhered in the desired position. The foil wrapper must, in this case, be soft and flexible, so that it does not interfere with the deformability of the sealing material.

A design of this type with a foil wrapper enclosing the sealing material is particularly suitable for a user friendly packaging. For example, a drain can be prepackaged in the sealing material. The drain can, in this case, be provided under the foil, wherein the packaged sealing material already provides a sealed off egress of the drain from under the foil.

Further, the foil wrapped prepackaged sealing material can be provided in a form of a band shaped strip. This design is particularly suitable for sealing along the edge or rim of a large surface area foil. If in this design the foil wrapper is provided on both sides of the band shaped strip with a self-adhering outer layer, then the strip shaped sealing material cannot only serve for the sealing along the edge of the foil, but at the same time, can serve for adhering of the foil upon the skin outer surface.

The sealing materials used herein are generally non-irritating to the skin, so that they can in given cases be applied directly upon the skin. Since the moisture content of the sealing material however leads to a softening of the skin outer surface after long exposure, it is preferred that the sealing material not be applied directly upon the skin. If the sealing material is permanently enclosed in a foil wrapper, then this foil wrapper protects the skin from softening. In other cases a protective foil is preferably provided directly upon the skin outer surface, which prevents the moisture of the sealing material coming into contact with the skin.

BRIEF DESCRIPTION OF THE DRAWINGS

In the following the invention will be described in greater detail with reference to the illustrative embodiments shown in the drawings. There is shown:

FIG. 1 Schematic top view of a device for sealing of a wound area,

FIG. 2 A cross-section along line II—II in FIG. 1,

In FIGS. 1 through 3 a vacuum sealing of a wound area is shown.

DETAILED DESCRIPTION OF THE INVENTION

Figure 3:
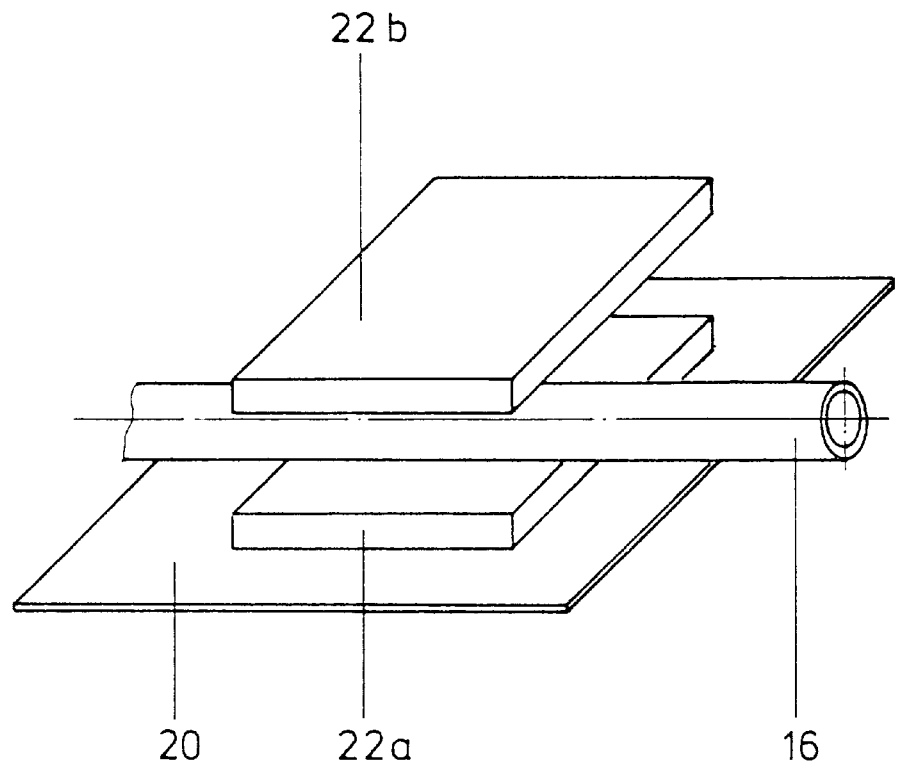
FIG. 3 A schematic of the application of the sealing material in the example according to FIG. 4, FIG. 4 A cross-section of a drain packaged with sealing material, and FIG. 5 Cross section of the device for sealing of a large surface area of a bodily extremity.

On the skin outer surface 10 a wound area 12 in the shape of a large surface area deep wound is to be treated. In the wound area 12 a porous foam insert 14 is introduced. A perforated end of a drain (Redon-Drain) 16 is introduced into a foam material insert 14 and is directed out of the wound area 12 over the skin outer surface 10. A water vapor permeable, airtight foil 18 is applied onto the wound area 12 for sealing off thereof. The edge of the foil 18 covers around the outside of the wound area 12 on all sides and then is adhered along its edge around the wound area. The outer end of the drain 16 is then connected to a suction pump, so that by means of the drain 16 and the foam material insert 14 a under-pressurization is achieved in the would area 12 under the foil 18, and the wound secretion is siphoned off via the pores of the foam material insert 14 and the drain 16.

In the edge area of the foil 18, in which the drain 16 exits between the skin outer surface 10 and the foil 18, the foil 18 cannot be adhered in sealing engagement upon the skin outer surface 10, so that in the area of the drain 16 between the skin outer surface 10 and the foil 18 non-sealed areas occur, which make difficult or prevent the achievement and maintenance of the under-pressurization in the wound area 12. These non-sealed areas are closed off using the sealing material 22, which fills the interstitial areas between the skin outer surface 10, the drain 16 and the foil 18. The sealing material 22 is an easily deformable, but not flowing material, in particular a silicone, a hydro-colloid or a hydrogel. The sealing material 22 can, on a basis of its gelatinous consistency, be pressed into the interstitial space between the skin outer surface 10, drain 16 and the foil 18 and sealingly fills the interstitial spaces. The sealing material 22 exhibits at the same time a sufficient non-deformability, so that it does not flow toward the inside of the wound area 12 due to the pressure gradient resulting between the outer side and inner side of the foil 18 upon evacuation of the wound area, but rather remains in its sealing position.

FIG. 3 schematically shows the sealing of the drain exit channel by means of the sealing material 22 in a first embodiment. In order to prevent the moisture containing sealing material 22 from contacting the skin outer surface 10 and softening it, a protective foil 20 is first adhered upon the skin outer surface in the area, in which the drain 16 is guided toward the outside. Onto this protective foil 20 a first sheet 22a of the sealing material 22 is attached. Then the drain 16 is laid upon this first sheet 22a and covered with a second sheet 22b of the sealing material 22. The upper sheet 22b is then pressed downwards so that it bonds with the lower sheet 22a and the sealing material 22 of the two sheets 22a and 22b completely encloses the drain 16. Now the foil 18 can be positioned and adhered. The foil 18 is at this time pressed upon the sealing material 22 enclosing the drain 16, so that no leak remains, as shown in FIG. 2.

In order that the sealing material 22 maintains the ideal consistency and moisture content, the sheets 22a,b of the sealing material 22 are stored in air tight enclosures and are therein kept in readiness. The sheets 22a,b of the sealing material 22 can therefore be either stored in an air tight closed container or be enclosed in an air tight foil wrapper, which can be removed prior to use.

In a different embodiment the sealing material 22 can also be stored in an air tight resealable tube or pouch or bag and therein be maintained in readiness. In this case the drain 16 is laid upon the protective foil 20 after the adhesion of the protective foil 20, whereupon a suitable amount of the sealing material 22 is expelled from the tube or the pouch and is pressed in about the drain 16. Subsequently the foil 18 can be applied and be pressed in on the area of the sealing material 22 enclosed drain 16, so that the sealing material 22 fills all interstitial spaces and voids and leaks.

Figure 4:
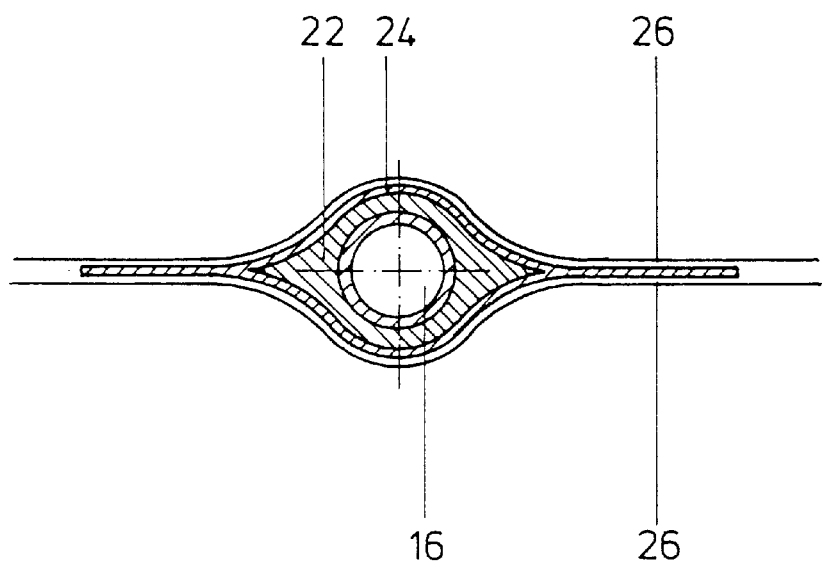

FIG. 4 shows a further embodiment, in which the drain 16 is already prepackaged with the sealing material 22. In an appropriate distance from the perforated end of the drain 16, the drain 16 is enclosed with a sufficient amount of the sealing material 22. The sealing material 22 is enclosed by a foil wrapper 24, which is provided on its outer surface with a self-adhering outer layer. In order to protect the adhesive foil wrapper 44 during storage, this is provided on both sides with a protective peel-off cover foil 26.

After the positioning of the drain 16 in the would area 12 the protective cover foil 26 is peeled off from the underside and the foil wrapper 24 is adhered in place for securing of the drain 16 upon the skin outer surface 10. Subsequently, the upper covering foil 26 is peeled off. Now the foil 18 can be provided whereby it sticks tight in the area of the sealing material 22 on the adhesive cover foil 26. The sealing material 22 is so deformed during the pressing on, that no voids or leaks remain between the foil 18 and the skin outer surface 10.

For covering and sealing of larger areas of the skin outer surface the direct adhering of the foil 18 upon the skin outer surface 10 can be found to be non-optimal or ineffective since folds or wrinkles of the skin outer surface 10 complicate and prevent an intimate application of the edge of the foil 18. For such applications the sealing material 22 is applied in the form of band shaped strips along the entire edge of the foil 18 between the skin outer surface 10 and the foil 18, in order to rule out any leaks, which would result from folds or contortions of the foil 18.

Preferably the sealing material 22 is therefore packaged as band shaped strips in a foil wrapper 24 coated on two sides with adhesive, wherein the adhesive coating of the foil wrapper 24 is protected by a peel off cover foil 26.

In this embodiment the self-adhering strips with the sealing material 22 can be first adhered upon the skin outer surface 10 and subsequently the foil 18 can be applied, which for its part is adhered by means of the self-adhesive strips of the sealing material 22. The strip shape sealing material 22 contained in the self-adhering foil wrapper 24 serves both for the securing of the foil 18 upon the skin outer surface 10 and for the sealing along the entire edge of the foil 18. The foil 18 can then be adhered for covering and for protection of the wound area 12, as is frequently necessary in emergency care. Of course, the drain 16 can be sealingly disposed under the foil 18 by means of the sealing material 22.

Figure 5:
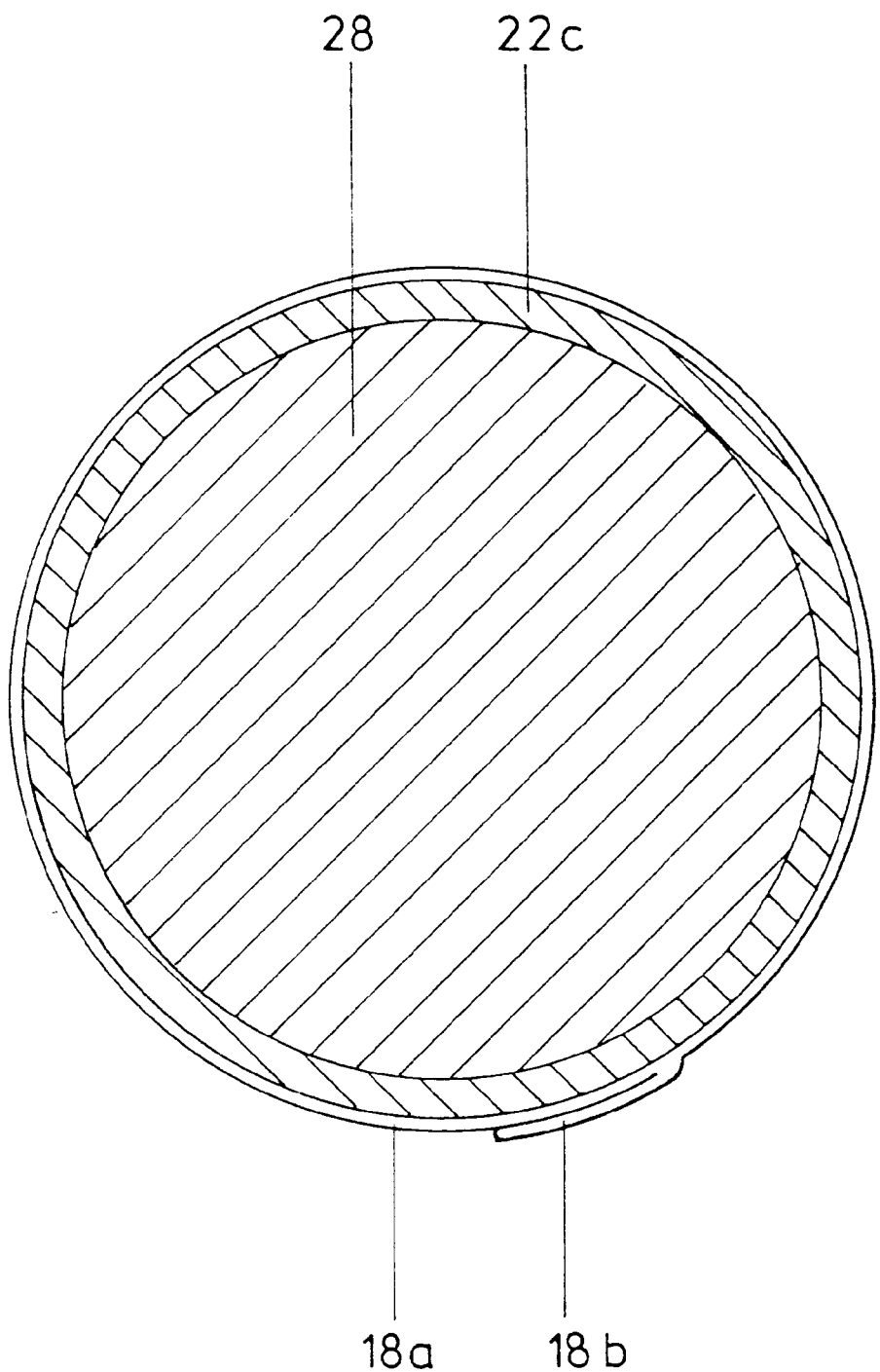

In FIG. 5 an example of an actual use of an embodiment is shown. In order to seal a large surface area injury of an extremity 28, for example of a leg, in the provisional emergency care, a sack-like or tubular foil 18*a* is pulled over the injured area of the extremity 28. Above or, as the case may be, above and below the wounded area of the extremity 28 a band shaped strip 22*c* of the sealing material 22 is adhered about the extremity 28. The open edge of the sack or tubular shaped foil 18*a* is tightened around the strip 22*c* of the sealing material 22 and tightly adhered thereto. The remaining loose material 18*b* of the foil 18*a* is folded over and is fixed and closed by means of a cover or the like. The strip 22*c* of the sealing material 22 achieves a seal between the extremity 28 and the foil 18*a* over the entire circumference of the extremity 28 despite unevenness and folds in the skin outer surface 10.

What is claimed is:

1. A method for sealing a wound area with a wound area covering water vapor permeable and airtight foil, said method comprising:

forming a water vapor permeable and airtight foil having edges defining an area greater than the periphery of said wound to be covered, and adapted for being adhered along its edges around about the wound area onto the skin outer surface surrounding the wound;

applying a porous foam insert over said wound area;

obtaining a drain (16) having proximal and distal ends, applying said proximal end of said drain over said porous foam covered wound and connecting said distal end of said drain to a vacuum source distanced from said wound, applying an easily deformable, non-flowing sealing material (22) around said drain (16) for forming a leak-proof seal between said edge area of the foil (18), said drain (16) in said edge area, and skin outer surface (10) when said water vapor permeable and airtight foil is applied over the wound, said sealing material adapted for sealing off any unevenness between said edge area of said foil (18) and the skin outer surface (10), applying said water vapor permeable and airtight foil over said wound such that an edge of said foil is in contact with said sealing material, and applying a vacuum through said drain to cause a vacuum between said wound and said water vapor permeable and airtight foil.

2. A method according to claim 1, wherein the sealing material (22) is a silicone, hydro-colloid or lyogel.

3. A method according to claim 2, wherein said lyogel is a hydrogel.

4. A method according to claim 1, wherein the sealing material (22) is in the form of a strip and is provided along an entire edge of the foil (18) to be applied to the skin outer surface (10).

5. A method according to claim 1, wherein the foil (18) is in the form of a tube or a sack adapted for enclosing a bodily section of the patient, and wherein a strip of the sealing material (22) is provided along the area of the edge of the foil (18) as necessary for encircling said bodily section.

* * * * *